(12) United States Patent
Dong et al.

(10) Patent No.: US 10,285,655 B2
(45) Date of Patent: May 14, 2019

(54) IMAGING SYSTEM SUBJECT SUPPORT

(75) Inventors: Shufang Dong, Mayfield Heights, OH (US); Terrance Joseph Nemenz, Chesterland, OH (US); Patrick Cumpson, Chesterland, OH (US); Jeremy David Pettinato, Mentor, OH (US); Sriram Rajagopal, Mayfield Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 255 days.

(21) Appl. No.: 14/002,787

(22) PCT Filed: Mar. 9, 2012

(86) PCT No.: PCT/IB2012/051110
§ 371 (c)(1),
(2), (4) Date: Sep. 3, 2013

(87) PCT Pub. No.: WO2012/120477
PCT Pub. Date: Sep. 13, 2012

(65) Prior Publication Data
US 2013/0340165 A1  Dec. 26, 2013

Related U.S. Application Data

(60) Provisional application No. 61/450,680, filed on Mar. 9, 2011.

(51) Int. Cl.
| | |
|---|---|
| *A61B 6/00* | (2006.01) |
| *A61B 6/03* | (2006.01) |
| *A61B 6/04* | (2006.01) |
| *A61B 6/10* | (2006.01) |
| *A61B 5/055* | (2006.01) |

(52) U.S. Cl.
CPC .............. *A61B 6/105* (2013.01); *A61B 6/032* (2013.01); *A61B 6/102* (2013.01); *A61B 6/586* (2013.01); *A61B 5/055* (2013.01); *A61B 6/037* (2013.01); *A61B 6/04* (2013.01); *A61B 6/4441* (2013.01); *A61B 6/547* (2013.01)

(58) Field of Classification Search
CPC ...................... A61G 2203/72; A61G 2203/726
USPC ............................ 600/415; 187/269; 378/117
See application file for complete search history.

(56) References Cited

U.S. PATENT DOCUMENTS

| | | | |
|---|---|---|---|
| 4,131,802 A | 12/1978 | Braden et al. | |
| 6,986,179 B2 * | 1/2006 | Varadharajulu et al. | 5/611 |
| 7,379,533 B2 * | 5/2008 | Koertge | 378/117 |
| 7,697,971 B1 * | 4/2010 | Green et al. | 600/415 |

(Continued)

FOREIGN PATENT DOCUMENTS

WO   2007005011 A1   1/2007

*Primary Examiner* — Robert G Santos
*Assistant Examiner* — Myles A Throop

(57) ABSTRACT

A method includes receiving a subject support motion disable signal indicative of at least one of power removal of an imaging system, a collision of a horizontally moving tabletop of the imaging system, a decoupling of a horizontal motion drive system configured to horizontally drive the tabletop, or a collision of a vertically moving subject support of the imaging system, wherein a vertical motion drive system drives the subject support vertical motion, and disabling, in response to receiving the subject support motion disable signal, at least one of tabletop horizontal motion or subject support vertical motion.

18 Claims, 11 Drawing Sheets

(56) References Cited

U.S. PATENT DOCUMENTS

| | | | |
|---|---|---|---|
| 7,834,768 B2* | 11/2010 | Dixon et al. | 340/573.1 |
| 8,959,681 B2* | 2/2015 | Richards | 5/613 |
| 2003/0100824 A1* | 5/2003 | Warren et al. | 600/407 |
| 2005/0005356 A1* | 1/2005 | Zacharopoulos et al. | 5/601 |
| 2005/0114996 A1* | 6/2005 | Somasundaram | 5/601 |
| 2005/0129181 A1 | 6/2005 | Shinoda | |
| 2006/0058601 A1* | 3/2006 | Smith et al. | 600/407 |
| 2006/0167356 A1* | 7/2006 | Everett et al. | 600/407 |
| 2008/0135268 A1 | 6/2008 | Tadokoro et al. | |
| 2008/0172793 A1 | 7/2008 | Gagneur et al. | |
| 2008/0189856 A1* | 8/2008 | Toms et al. | 5/424 |
| 2008/0279333 A1 | 11/2008 | Sattler et al. | |
| 2009/0070936 A1 | 3/2009 | Henderson et al. | |
| 2009/0285364 A1 | 11/2009 | Caruba | |
| 2009/0313758 A1* | 12/2009 | Menkedick et al. | 5/618 |
| 2010/0121604 A1 | 5/2010 | Vaisburd et al. | |
| 2010/0275927 A1 | 11/2010 | Saracen et al. | |
| 2010/0287697 A1 | 11/2010 | Ahlman | |
| 2010/0319128 A1* | 12/2010 | Kuro et al. | 5/601 |
| 2010/0329414 A1* | 12/2010 | Zhu et al. | 378/4 |
| 2013/0345543 A1* | 12/2013 | Steibel et al. | 600/407 |

* cited by examiner

IMAGING SYSTEM SUBJECT SUPPORT

CROSS REFERENCE TO RELATED APPLICATIONS

This application is a national filing of PCT application Serial No. PCT/IB2012/051110, filed Mar. 9, 2012, published as WO 2012/120477 A2 on Sep. 13, 2012, which claims the benefit of U.S. provisional application Ser. No. 61/450,680 filed Mar. 9, 2011, which is incorporated herein by reference.

FIELD OF THE INVENTION

The following generally relates to an imaging system subject support configured to carry an object or subject before, during and/or after scanning the object or subject, and is described with particular application to computed tomography (CT). However, the following is also amenable to subject supports for other imaging modalities, including, but not limited to magnetic resonance imaging (MRI), positron emission tomography (PET), single photon emission tomography (SPECT), X-ray, and/or other imaging modalities.

BACKGROUND OF THE INVENTION

A computed tomography (CT) scanner includes a rotating portion rotatably supported by a stationary portion. The rotating portion supports an x-ray tube, which emits radiation that traverses an examination region and an object or a subject therein, and a detector array that detects radiation traversing the examination region and generates projection data indicative of the detected radiation. A subject support supports the object or subject in the examination region before, during and/or after scanning, for example, for loading the object or subject, feeding the object or subject into and removing the object or subject from the examination region, and unloading the object or subject. A reconstructor reconstructs the projection data and generates volumetric image data indicative of the portion of the object or subject in the examination region.

The subject support includes a base, which is affixed to the floor of the examination room and is configured to move vertically, under electronic control, with respect to the floor, and a tabletop, which is affixed to the base and is configured to translate horizontally, under electronic control or manually via a user, with respect to the base, in and out of the examination region before, during and/or after scanning. The scanner also includes circuitry to prevent and/or controllably stop electronically controlled vertical and horizontal motion respectively of the base and the tabletop, for example, in response to controlled and uncontrolled removal of power, to prevent a collision, to mitigate a detected collision, or in response to a fault in the subject support drive system. Such circuitry has been configured so that the stopping of the moving subject support complies with certain standards and is comfortable to a patient.

By way of example, IEC 60601 revs 1 and 2 require stopping an electronically controlled moving tabletop in ten millimeters (10 mm) and IEC 60601 rev 3 requires stopping an electronically controlled moving tabletop in twenty-five millimeters (25 mm), both within a half a second (0.5 s) from the time of removal of power and with a one hundred and thirty-five kilogram (135 kg) load, with subsequent placement of the tabletop in a free float state. A conventional tabletop has been configured to translate at speeds up to two hundred millimeters per second (200 mm/s) and satisfy the above-noted IEC requirements by removing power supplied to the tabletop motor and letting the tabletop coast to a stop.

Unfortunately, such braking at higher speeds would add to overall system cost due to the higher peak power requirement and may also introduce discomfort and/or risk to lighter weight patients if the braking current is determined for a heavier load. Furthermore, at higher speeds, if horizontal and vertical collisions or drive chain failures cannot be detected in time, such motion can cause damage to the subject support and/or objects external to the subject support. Furthermore, attaching subject support accessories to the subject support may change allowable vertical and/or horizontal motion of the subject support, which may lead to collisions for a given the collision envelope that otherwise would not occur. Moreover, conventional imaging systems may provide less then desired support and/or mechanisms for securing certain accessories to the subject support.

SUMMARY OF THE INVENTION

Aspects of the present application address the above-referenced matters and others.

According to one aspect, a method includes receiving a subject support motion disable signal indicative of at least one of power removal of an imaging system, a collision of a horizontally moving tabletop of the imaging system, a decoupling of a horizontal motion drive system configured to horizontally drive the tabletop, or a collision of a vertically moving subject support of the imaging system, wherein a vertical motion drive system drives the subject support vertical motion, and disabling, in response to receiving the subject support motion disable signal, at least one of tabletop horizontal motion or subject support vertical motion.

According to another aspect, an imaging system includes a radiation source that emits radiation that traverses an examination region, a detector array, located opposite the source across the examination region, that detects radiation traversing the examination region, and a subject support configured to support an object or subject for scanning. The subject support includes a base configured for vertical motion and a tabletop configured for horizontal motion, wherein the tabletop is slidably mounted to the base. The system further includes a component for disabling at least one of subject support horizontal or vertical motion in response to a predetermined event of the imaging system.

According to another aspect, an imaging system includes a console for controlling the imaging system, a radiation source that emits radiation that traverses an examination region, a detector array, located opposite the source across the examination region, that detects radiation traversing the examination region, and a subject support configured to support an object or subject for scanning. The subject support includes a sensor configured to sense physical attachment of a subject support accessory to the subject support and identify a type of the accessory, wherein the console identifies a subject support collision envelope for the subject support based on the identified type of the accessory and employs the identified collision envelope when one of horizontally or vertically moving the subject support.

According to another aspect, an imaging system includes a subject support configured to support an object or subject for scanning. The subject support includes a base configured for vertical motion and a tabletop slidably mounted to the base and configured for horizontal motion. The tabletop is electrically non-conductive.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
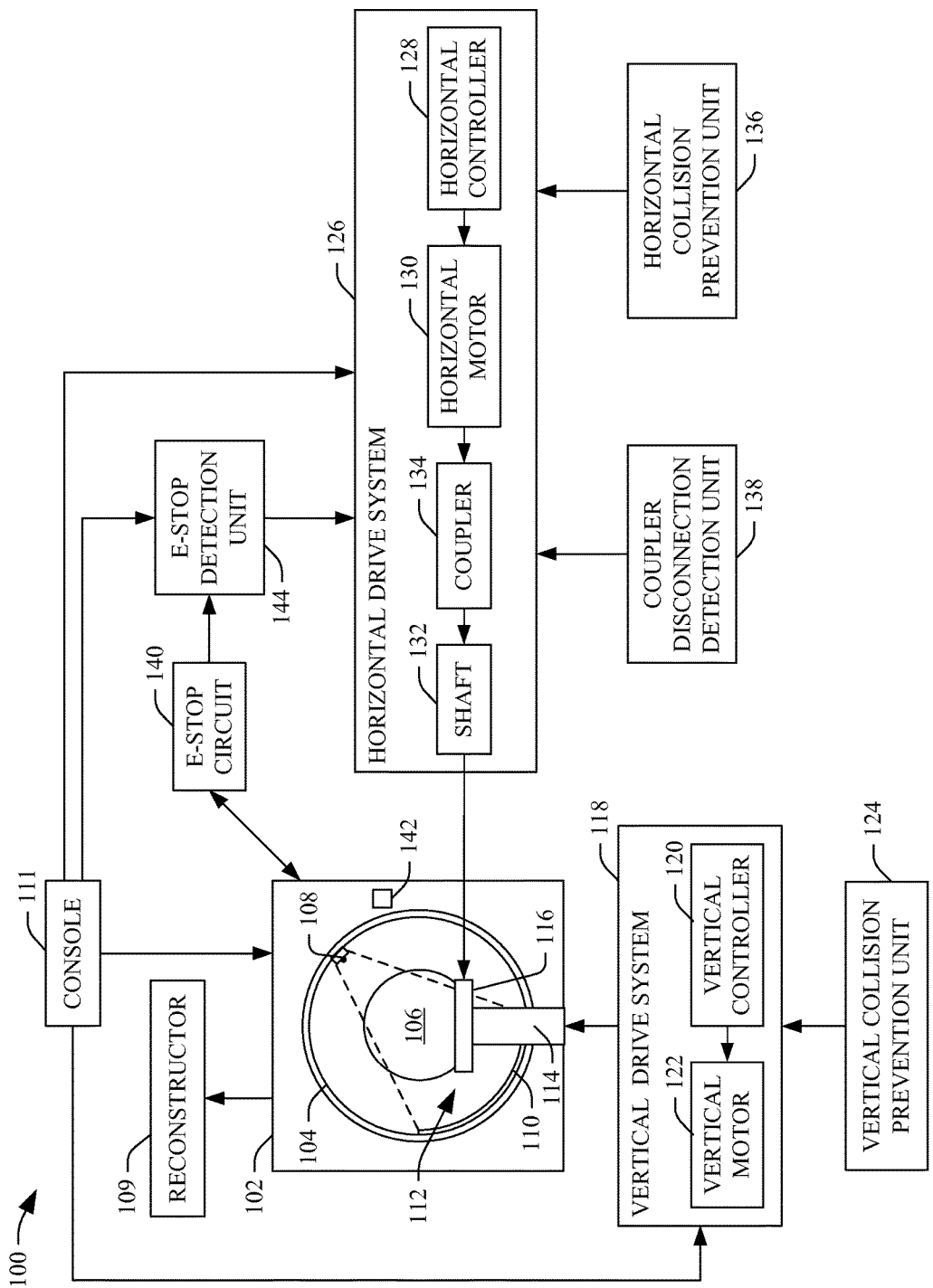
FIG. 1 schematically illustrates an imaging system in connection with an optional E-stop detection unit, a horizontal collision prevention unit, a vertical collision prevention unit, a couple disconnection detection unit, and a subject support.

FIG. 1 schematically illustrates an imaging system 100 such as a computed tomography (CT) scanner. The imaging system 100 includes a stationary gantry 102 and a rotating gantry 104, which is rotatably supported by the stationary gantry 102. The rotating gantry 104 rotates around an examination region 106 about a longitudinal or z-axis.

A radiation source 108, such as an x-ray tube, is supported by and rotates with the rotating gantry 104 around the examination region 106. The radiation source 108 emits radiation that is collimated by a source collimator to produce a generally fan, wedge, cone, or otherwise shaped radiation beam that traverses the examination region 106. A radiation sensitive detector array 110 includes a one or two dimensional array of detector pixels that respectively detect radiation that traverses the examination region 106 and generates an electrical signal indicative of the detected radiation.

A reconstructor 109 reconstructs the signal generated by the detector array 110 and generates volumetric image data indicative of the examination region 106. A general purpose computing system serves as an operator console 111, and includes an output device such as a display, an input device such as a keyboard, mouse, and/or the like, one or more processor and computer readable storage medium. The console 111 allows the operator to control operation of the system 100, for example, selecting scan protocols, initiating scanning, etc.

A subject support 112, such as a patient couch, supports an object or subject in the examination region 106. The subject support 112 includes a base portion 114 and a tabletop 116. The base portion 114 is affixed to or rests on the floor in the examination room and is configured to move vertically down and up for patient loading and unloading and for positioning the patient at a suitable height for scanning, for example, based on the region to be scanned, the iso-center of the scan field of view, and/or otherwise. A vertical drive system 118 includes a vertical controller 120, which drives a vertical motor 122 that drives the mechanism that raises and lowers the base 114.

A vertical collision prevention unit 124 can selectively stop controlled vertical motion of the subject support 112. As described in greater detail below, in one instance this includes sensing when the subject support 112 collides with an object during vertical motion and disabling or stopping the vertical controller 120 from further driving the vertical motor 122 in response thereto. Note that the use of vertical with respect to the drive system 118, the controller 120, the motor 122 and the collision prevention unit 124 refers to the vertical (up and down) motion and not any particular special orientation of the components.

The tabletop 116 is moveably affixed to the base portion 114 and is configured to move horizontally in and out of the examination region 106 before, during and after scanning for patient loading, patient scanning and patient unloading. A horizontal drive system 126 includes a horizontal controller 128, which drives a horizontal motor 130 that is coupled to an end of an elongate shaft 132 via a coupler 134, wherein a second end of the shaft 132 is coupled to the tabletop 116 via a yoke bridge of the like. Generally, the horizontal controller 128 drives the motor 130, which turns the coupler 134 and hence the shaft 132, which, in turn, horizontally translates the tabletop 116.

As described in greater detail below, the tabletop 116 may include or be associated with various features such as being electrically non-conductive, being grounded, being isolated, being configured to receive an electrically non-conductive apparatus on which the patient lies, including static and/or removable added patient support, including mechanism for attaching, securing, removing, identifying, etc. one or more accessories such as headrests, footrests, etc., and/or to the attachment and/or removal of one or more accessories such as identifying collision envelopes, recommending collision envelopes, mitigating collisions, etc. automatically and/or in response to operator confirmation.

A horizontal collision prevention unit 136 can selectively stop horizontal motion of the subject support 112. As described in greater detail below, in one instance this includes sensing when the subject support 112 collides with an object during horizontal motion and disabling or stopping driving of the horizontal motor 130 in response thereto. A coupler disconnection detection unit 138 can also selectively stop driving of the horizontal motor 130. As described in greater detail below, in one instance this includes sensing a disconnection between the coupler 134 and at least one of the motor 130 or the shaft 132, and disabling or stopping driving of the horizontal motor 130 in response thereto. Note that the use of horizontal with respect to the drive system 126, the controller 128, the motor 130 and the collision prevention unit 136 refers to the horizontal (back and forth along the z-axis) motion and not any particular special orientation of the components.

An emergency stop (E-stop) circuit 140 includes an electrical circuit the senses uncontrolled and/or user controlled removal of power from one or more components of the system 100. In the illustrated embodiment, the E-stop circuit 140 is a dedicated normally closed (or open) electrical current loop, interconnecting various emergency stop switches of the system 100. One such switch 142 is shown located on the stationary gantry 102. Other switches may be located inside and outside of the examination room, at the console 111, and/or other places. Opening the switch 142 disrupts electrical current flow in the E-stop circuit 140. With a normally closed circuit, electrical current will flow in the E-stop circuit 140 when power is supplied and no E-stop switch is in an open state. Current flow is disrupted in response to electrically opening the E-stop circuit, for example, through activating the switch 142.

An E-stop detection unit 144 can selectively stop driving of the horizontal motor 130. As described in greater detail below, in one instance this includes monitoring the E-stop circuit 140 and sensing disruption of electrical current flow in the E-stop circuit 140, and disabling or stopping the horizontal controller 128 from driving of the horizontal motor 130 and/or removing motor regenerated current from the coil of the horizontal motor 130 in response thereto, and, optionally, placing the tabletop in a free float state after the tabletop stops and/or lapse of a predetermined time.

Figure 2:
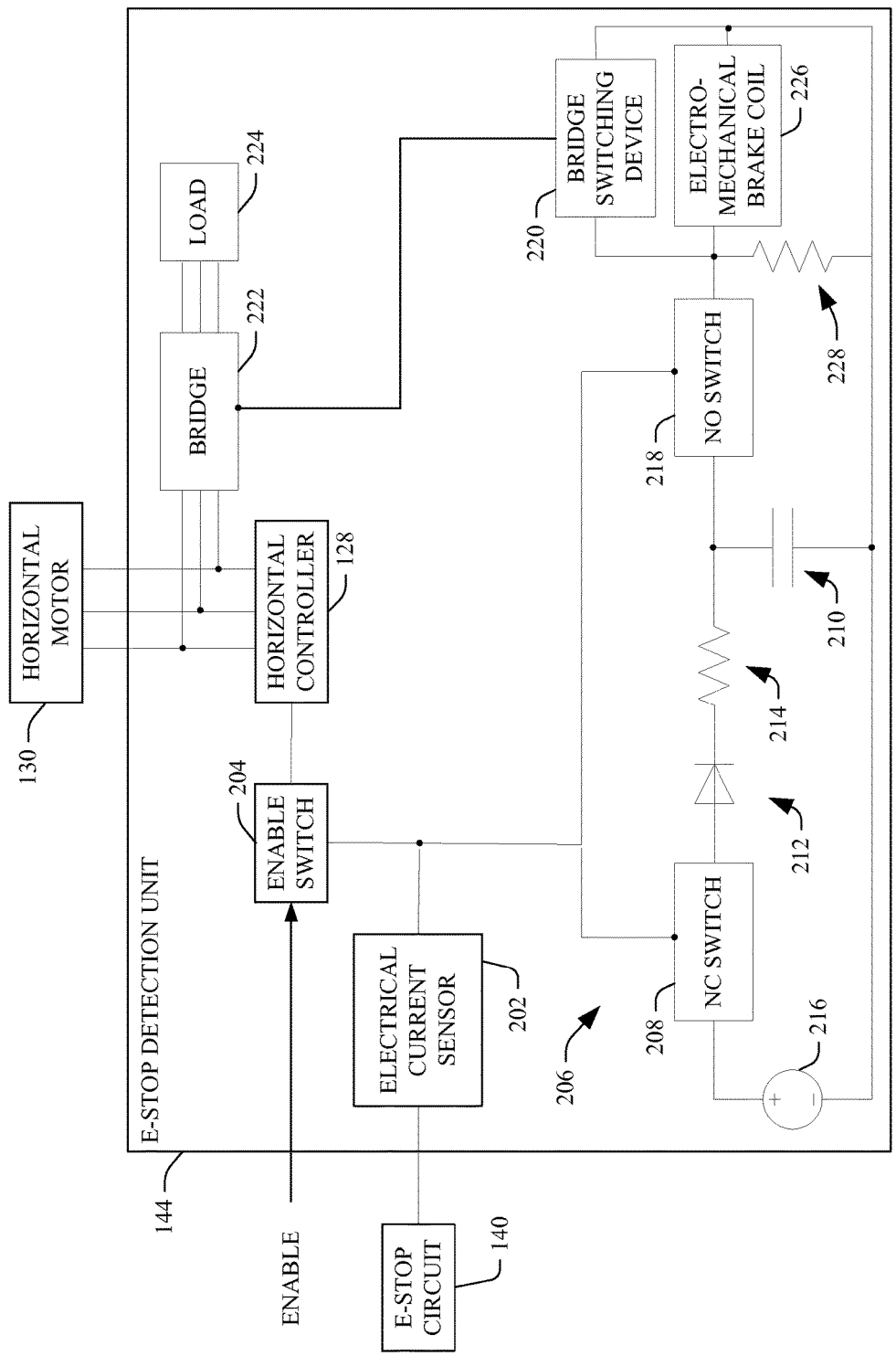
FIG. 2 schematically illustrates an example E-stop detection unit that can be used in connection with the imaging system of FIG. 1.

FIG. 2 illustrates a non-limiting example of the E-stop detection unit 144 in connection with sub-portion of the E-stop circuit 140 and the horizontal drive system 126. In this example, the horizontal motor 130 is a three (3) phase permanent magnet AC (alternating current) servo motor. In other embodiments, other motors such as a brushless DC motor, a brush DC permanent motor, and/or other motor can be used. Furthermore, it is to be understood that the following implementation of the E-stop detection unit 144 is provided for explanatory purposes and is not limiting, and other implementation are also contemplated herein.

The E-stop detection unit 144 includes an electrical current sensor 202 that senses electrical current flow in the E-stop circuit 140 and a change thereof in electrical state. In the illustrated embodiment, the electrical current sensor 202 includes a hall-effect sensor that converts E-stop loop current flow to a high potential (E-Stop-Ok) signal and no current flow into a low potential (E-Stop-Not-Ok) signal. The output signal of the electrical current sensor 202 is electrically connected to the subject support 112 as a direct electrical current input, as described in further detail next.

For example, the signal from the electrical current sensor 202 is fed to an enable switch 204, which enables the horizontal controller 128 to drive the horizontal motor 130 when the enable switch 204 receives both, an enable signal(s) and an E-Stop-Ok signal. If either the enable signal or the E-Stop-Ok signal is not received (or the E-Stop-Not-Ok signal is received), the horizontal controller 128 is disabled from driving the horizontal motor 130. In one instance, this includes disabling the output of the horizontal controller 128 such that it is electrically disconnected from the horizontal motor 130, for example, within one cycle of the drive sampling period, or within a range of a half a millisecond (0.5 ms) to ten milliseconds (10 ms) such as three-quarters of a millisecond (0.75 ms) to seven milliseconds (7 ms), one millisecond (1 ms) to four milliseconds (4 ms), and/or other range, for example, depending on the drive cycling period.

The signal from the electrical current sensor 202 is also fed to motor coil shorting circuitry 206, which closes and opens a normally closed (NC) switch (e.g., a MOSFET (Metal Oxide Semiconductor Field Effect Transistor in this example) 208, and opens and closes a normally open (NO) switch (e.g., a MOSFET) 218 to turn off a normally the NO switch 218.

When the NC switch 208 is closed and the NO switch 218 is open, a charge storage device such as a capacitor 210 is charged via a DC (direct current) power source 216 or other power source. As shown, the capacitor 210 can be charged through a diode 212 and a charging resistor 214. However, other implementations are also contemplated herein. With the switches in these states, no electrical current flows through the NO switch 218 to a bridge switching device 220 (e.g., an IGBT (Insulated Gate Bipolar Transistor), a SSR (Solid State Relay, or the like), and so a normally open bridge 222 (three (3) phase in the illustrated example) configured to electrically connect the coils of the horizontal motor 130 to a resistive load 224 (e.g., a resistor) is not closed or activated. The bridge 222, when open, is configured to allow the horizontal controller 128 to drive the horizontal motor 130, when the enable switch 204 device 210 receives both the enable signal and the E-Stop-Ok signal.

When the NC switch 208 is open and the NO switch 218 is closed, the charge storage device 210 no longer charges. Instead, the charge in the charge storage device 210 supplies power to the NO switch 218, and electrical current flows to the bridge switching device 220, which closes and enables the bridge 222 to electrically connect the coils of the motor to the resistive load 224 (e.g., a resistor). Recall from above, the enable switch 204 also opens in response to the E-Stop-Not-Ok signal, and the horizontal controller 128 does not drive the horizontal motor 130. However, the motor regenerating current from the coil of the horizontal motor 130 will flow through to bridge 222 to the resistive load 224, directly or through one or more components such as a rectifier, to remove the regenerated electrical current via dissipation as heat, which slows down and stops the horizontal motor 130. Where an external ancillary electro-mechanical brake (not visible) is used, the capacitor 210 is also used to power the coil of the electro-mechanical brake coil 226 for the ancillary brake to further brake the horizontal motor 130. A discharging resister 228 facilitates discharging the charge capacitor 210. Once the capacitor 210 is fully discharged, the bridge 222 opens again, and the external brake (if one is used) is released, and the motor 130 transitions into a free float state in which the tabletop can be easily moved by authorized personnel, for example, by pushing and/or pulling on the tabletop 116.

It is to be understood that the above applies to controlled E-stop circuit 140 state changes, for example, where an operator of the system physically activates an E-stop switch 142, for example, by pressing, pulling or activating the switch 142 however the switch 142 is activated, and to uncontrolled E-stops, for example, during uncontrolled loss or removal of power. As such, the E-stop detection unit 144 provides a passive, safety circuit in various power loss scenarios.

In the illustrated embodiment, the NC and NO switches 208 and 218 are low current charging and discharging switch devices, and the bridge 222 is used for high current flow of motor regenerating braking. Where the level of the motor regenerating braking current is lower, the bridge 222 may alternatively be a low current device such as a MOSFET or the like. Furthermore, where the horizontal motor 130 is a brush DC permanent motor, a single phase switching device bridge or other bridge can be used in place of the three phase switching device bridge 222.

It is to be appreciated that the use of the dedicated E-stop circuit 140 shortens the time it takes to disable the horizontal controller 128 and short horizontal motor 130 relative to a non-dedicated emergency stop circuit which senses emergency situations. Furthermore, the MOSFET, SSR, and IGBT devices are all semiconductor devices that can be turned on or off in nano-seconds or micro-seconds, so the response rate of the regenerating braking is essentially guaranteed.

Generally, the values of the capacitor 210, the braking resistor 214, the brake coil 226, the charging resistor 214, and the discharging resistor 228 are such that the horizontal motion stops within a predetermined distance (e.g., from 1 to 50 mm, such as within 50 mm, 25 mm, 10 mm, 7 mm 1 mm, etc.) and/or a predetermined time (e.g., 1-10 ms, such as 5, 4, 3, 2, or 1 ms). The following provides an example approach for determining various component parameters such as motor and brake electrical and mechanical parameters subject to the patient load, speed, stop distance and/or other criteria. In one instance, trade-offs between the peak deceleration level of motor dynamic braking which impacts patient safety and comfort in tabletop can be considered.

In this example, the parameters are determined based on EQUATION 1:

$$M\overline{X} = -\frac{K_e K_f}{R}\dot{X}, \qquad \text{EQUATION 1}$$

wherein $K_e$ represents the back electric motive force (EMF) coefficient of the motor Y, $K_f$ represents the torque or linear force constant of the motor Y, R represents the total resistance of the motor resistance and the braking resistor resistance, M represents the inertia of the mechanical system and motor, $\overline{X}$ represents the acceleration of the motion, and $\dot{X}$ represents the speed of the motion.

From EQUATION 1, tabletop stop distance with pure dynamic braking can be determined based on EQUATION 2:

$$X_\infty = \frac{MR}{K_e K_f}\dot{X}_o, \qquad \text{EQUATION 2}$$

wherein $X_\infty$ represents the tabletop stop distance after the E-stop button is pushed or system power is removed, and $\dot{X}_o$ represents the tabletop initial speed. From EQUATION 2, the stop distance is linearly proportional to the initial travel speed, proportional to the travelling inertia and circuit resistance, and counter-proportional to the motor's back EMF and torque constant. The initial peak deceleration of the dynamic braking can be determined based on EQUATION 3:

$$\overline{X}_o = -\frac{K_e K_f}{MR}\dot{X}_o, \qquad \text{EQUATION 3}$$

wherein $\overline{X}_o$ represents the initial peak deceleration level, and $\dot{X}_o$ represents the initial peak speed.

From the above equations, higher initial speed and motor back EMF and torque constant will cause higher initial peak deceleration, which affects the patient comfort dramatically, and higher inertia and resistance will cause smaller initial deceleration level. Also from the above equations, the deceleration level is linearly reduced to zero as the speed approaches to zero. If the initial peak deceleration level of dynamic braking is too high for patient comfort to achieve the given stop distance with regard to the given initial tabletop speed, an external ancillary brake can be used to smooth the deceleration level, which will result in a more even deceleration level across the whole braking process.

The cut-off frequency of the dynamic braking system is $$\frac{K_e K_f}{MR},$$

and its reverse multiplied by $2\pi$, or $$\frac{2\pi MR}{K_e K_f},$$

represents the time constant of the dynamic braking system, which can be used to guide the parameter selection of capacitor charging circuit and discharging circuit for external brake and motor coil shorting.

Figure 3:
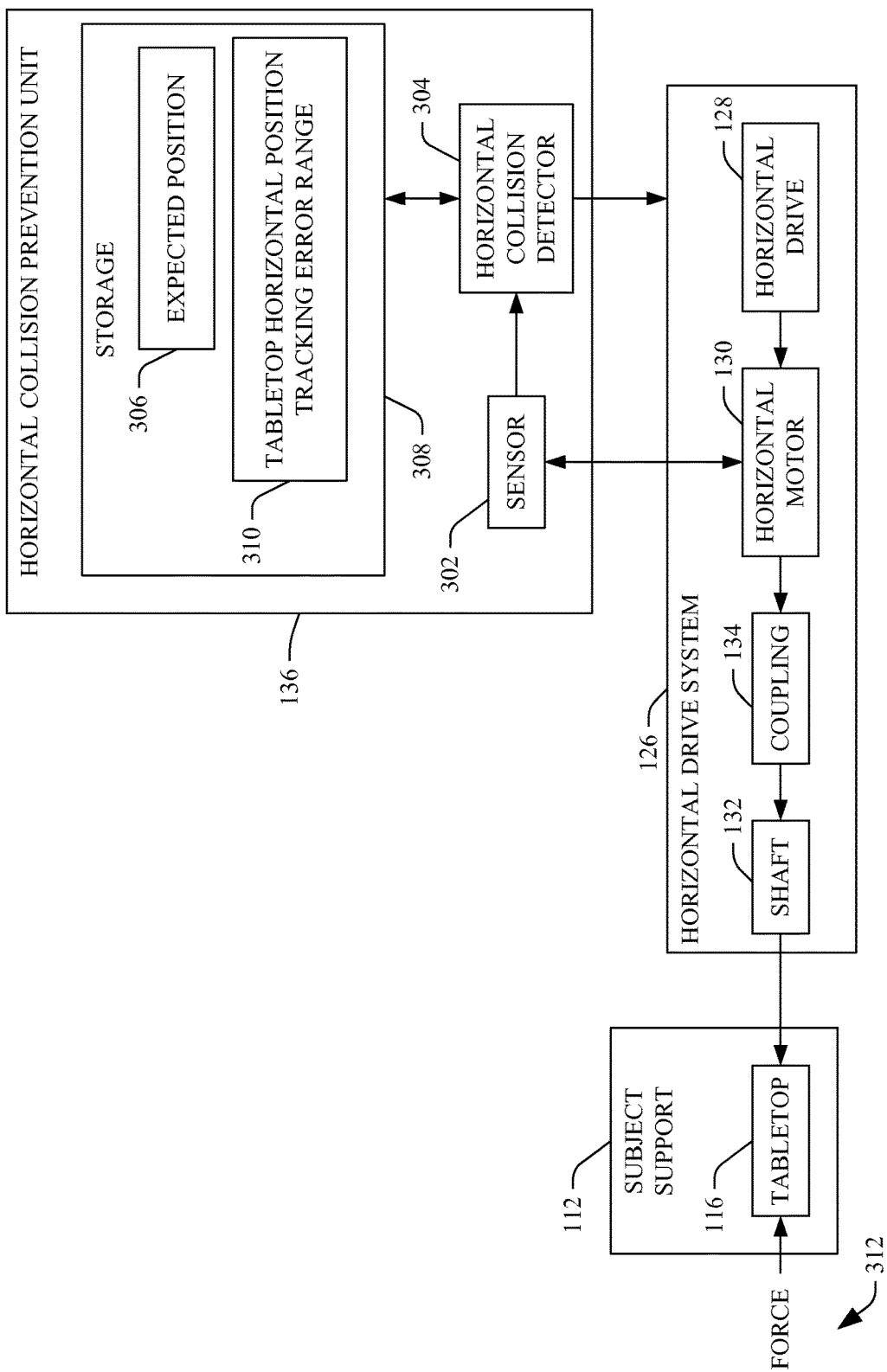
FIG. 3 schematically illustrates an example horizontal collision prevention unit that can be used in connection with the imaging system of FIG. 1.

FIG. 3 schematically illustrates an example of the horizontal collision prevention unit 136 in connection with the horizontal drive system 126 and the subject support 112. Generally, the horizontal drive 128 is programmed to drive the horizontal motor 130 with sufficient electrical current or torque so as to achieve planned motion of the tabletop 116 for scanning, including acceleration and deceleration for overcoming drive chain friction and patient load.

The illustrated horizontal collision prevention unit 136 includes a sensor 302 configured to sense motor position. A suitable sensor includes, but is not limited to, a rotary encoder, which can be affixed to the motor shaft and coverts motor shaft rotational motion into a linear position of the tabletop 116. A horizontal collision detector 304 compares the sensed position of the tabletop 116 with an expected tabletop position 306 from storage 308 (e.g., local or remote memory) and generates a difference signal indicative of a difference between the expected position 308 and the sensed position. The horizontal collision prevention unit 136 compares the difference signal with a tabletop horizontal position tracking error range 310 from the storage 308. The horizontal collision prevention unit 136, in responses to the difference signal falling outside of the range 310, sends a control signal to the horizontal drive system 126, which disables or stops the horizontal drive 128 from driving the horizontal motor 130, thereby stopping active translation of the tabletop 116.

In one instance, the tabletop horizontal position tracking error range 310 is a predetermined fixed value, which is independent of tabletop motion velocity. In another instance, the tabletop horizontal position tracking error range 310 is variable in that the position error width of the range depends on tabletop motion velocity. In this instance, the variable tabletop horizontal position tracking error range 310 can be represented as a mathematical function or algorithm, where the horizontal collision detector 304 dynamically calculates the tabletop horizontal position tracking error range 310 in response to receiving a signal (e.g., from the console or otherwise) indicative of the velocity of the tabletop 116 for a scan, which can be determined based on the imaging protocol selected for the scan or otherwise. In another example, the variable tabletop horizontal position tracking error range 310 is included in a look up table (LUT), which cross references or maps tracking error range values with tabletop velocity. The expected tabletop position 306 can be determined based on the selected scan protocol or otherwise.

An example scenario that may result in the difference signal falling outside of the range 310 is when an external force 312 is applied to the tabletop 116 and inhibits or slows tabletop motion. Such a situation may occur when an object such as a portion of a human, equipment, etc. is in the path of the tabletop motion and impedes the motion. In this scenario, the object applies the force against the moving tabletop 116, the tabletop 116 slows down or stops moving, the sensor 302 senses the position error, which accumulates over time, and, when the difference signal falls outside of the position error range 310, the horizontal collision detector 304 sends the signal which disables or stops the horizontal drive 128 from driving the horizontal motor 130. Where no such object impedes the path or where the object is removed from the path prior to the position reaching the position error range 310, the horizontal collision detector 304 does not prevent that horizontal drive 128 from driving the horizontal motor 130.

Figure 4:
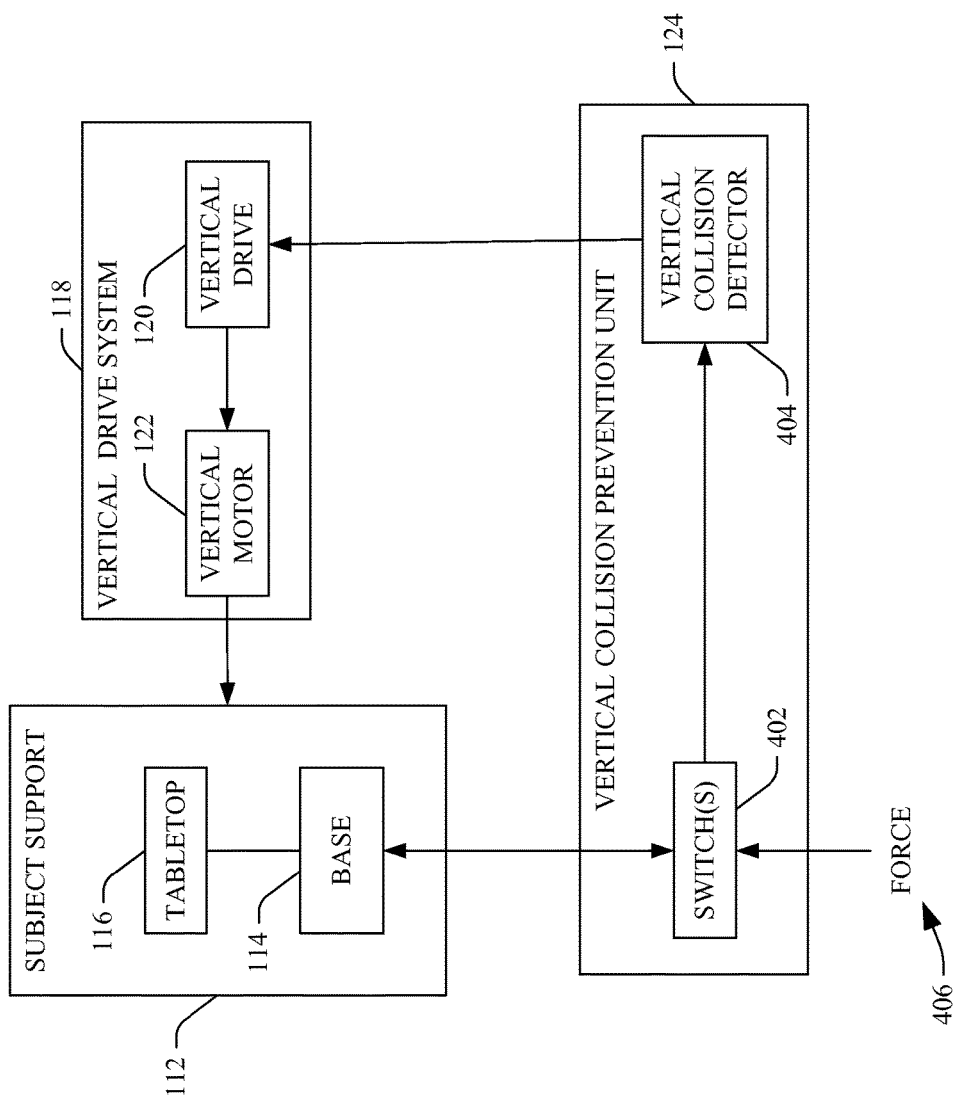
FIG. 4 schematically illustrates an example vertical collision prevention unit that can be used in connection with the imaging system of FIG. 1.

FIG. 4 schematically illustrates an example of the vertical collision prevention unit 136 in connection with the vertical drive system 118 and the subject support 112. Generally, the vertical drive is programmed to drive the vertical motor 122 to lower and raise the base 114 and hence the tabletop 116 for patient loading and unloading.

The vertical collision prevention unit 136 includes at least one switch 402 affixed to the tabletop 116 and/or base 114 between the tabletop 116 and/or base 114 and the floor to which the subject support 112 is attached such as on outside covers of the subject support 112. Suitable switches include normally open or normally closed switches that change state, or transition to the closed or open state, upon receiving an external force. Such sensing can be through physical contract, for example, where the one or more switches includes contact tape or spring loaded switches, or through other mechanisms such as optically, magnetically, etc.

A vertical collision detector 404 detects when the one or more switches 402 are switched and change state from a normal operating state to a tripped state, and generates and conveys a control signal which causes the vertical drive 120 to disable or stop driving the vertical motor 122 and hence the base 114 and tabletop 116 in the vertical direction. The vertical collision detector 404 does not generate the signal or does not generate a signal that causes the vertical drive 120 to stop driving the vertical motor 122 in response to the switch state remaining in the normal operating state.

An example scenario may include electronically lowering the base 114 and hence the tabletop 116, where an object such as a chair or other object located between the tabletop 116 and the floor, and the one or more switches 142 affixed to the tabletop 116 physically contacts the chair, which exerts a counter external force 406. In this instance, the vertical collision detector 404 detects the change in the state of the one or more switches 402 and generates and sends the control signal to the vertical drive 120 to stop the vertical drive from driving the vertical motor 122 and hence the tabletop 116 into the chair.

With respect to FIGS. 3 and 4, electrical current, velocity, and/or other parameter may additionally or alternatively used to detect a collision.

Figure 5:
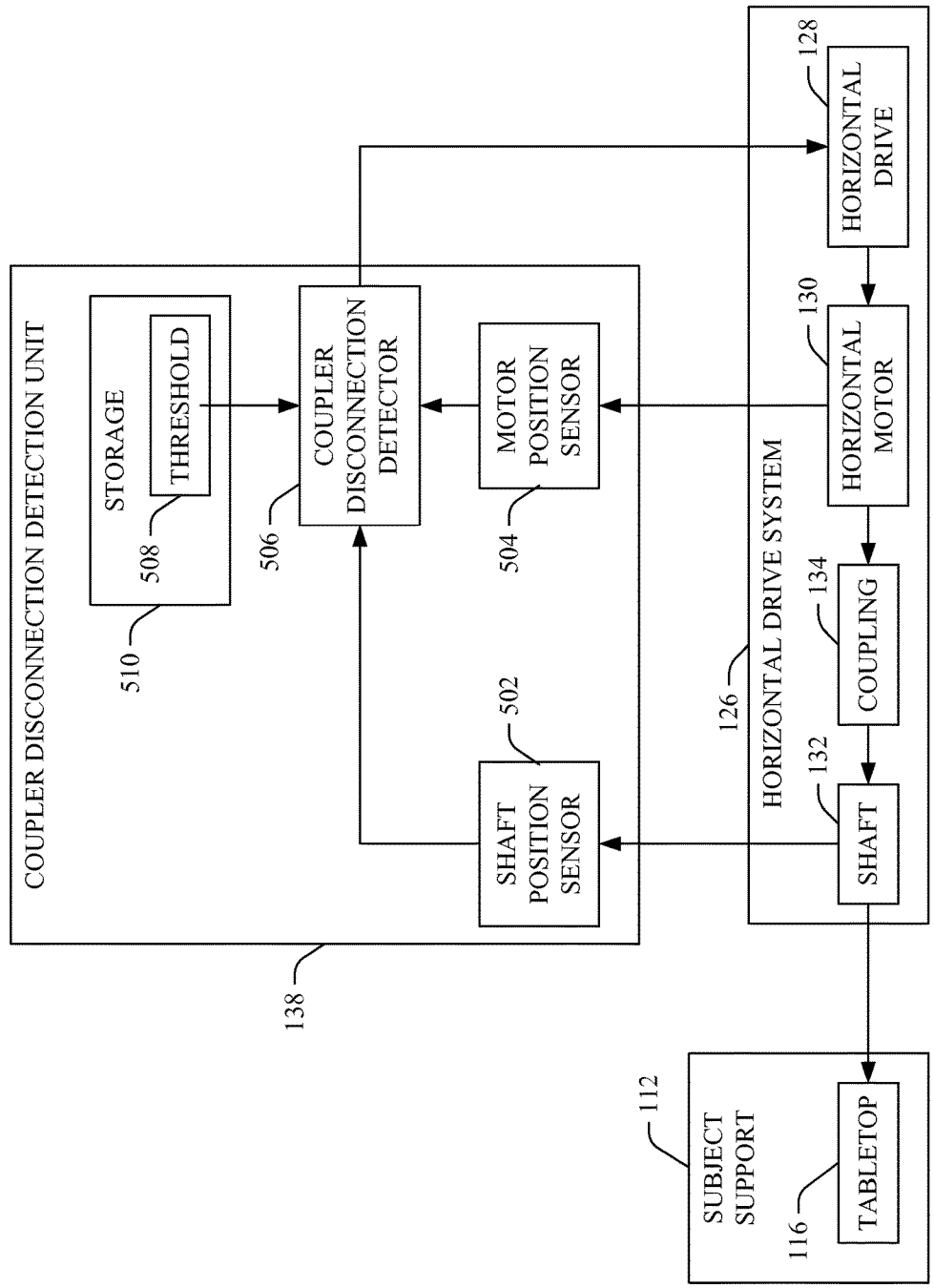
FIG. 5 schematically illustrates an example coupler disconnection detection having multiple position sensors and that can be used in connection with the imaging system of FIG. 1.

FIG. 5 schematically illustrates an example of the horizontal drive coupler disconnection detection unit 138 in connection with the horizontal drive system 126 and the subject support 112. As discussed above, the horizontal controller 128 drives the horizontal motor 130 (which is coupled to the shaft 132 via the coupler 134) which drives the shaft 132 to translate the tabletop 116.

The illustrated horizontal drive coupler disconnection detection unit 138 includes at least a shaft position sensor 502 and a motor position sensor 504. The shaft position sensor 502 determines a horizontal tabletop position at that shaft 132 and generates a first tabletop position signal based thereon, and the motor position sensor 504 determines a horizontal tabletop position at that the horizontal motor 130 and generates a second tabletop position signal based thereon. In the illustrated embodiment, the sensors 502 and 504 include rotary encoders that convert the rotational motion of the shaft and motor into linear position. Generally, using rotary encoders may reduce overall system cost relative to a configuration with linear encoders and eliminates the need for a gear reducer or belt drive.

The coupler disconnection detector 506 determines a difference signal indicative of a position difference between the positions sensed by the sensors 502 and 504. The coupler disconnection detector 506 compares the difference signal with a predetermined position difference threshold 508 from storage 510. The coupler disconnection detector 506, in response to the difference signal meeting and/or exceeding the predetermined position difference threshold, conveys a signal to the horizontal drive 128, which, in response thereto, disables or stops driving the horizontal motor 130. Otherwise, the coupler disconnection detector 506 does not convey the signal.

An example scenario may include a situation in which the coupling between the shaft 132 and the coupler 134 and/or the horizontal motor 130 and the coupler 134 becomes disconnected such that the motor 130 no longer causes the shaft 132 to rotate or rotate correctly and hence the tabletop 116 to translate in accordance with the motion profile for the scan. In this instance, the difference signal will be become larger over time and the horizontal drive 128, in response to receiving a difference signal that indicates that the difference signal meets and/or exceeds the predetermined position difference threshold 508, stops driving the horizontal motor 130.

Figure 6:
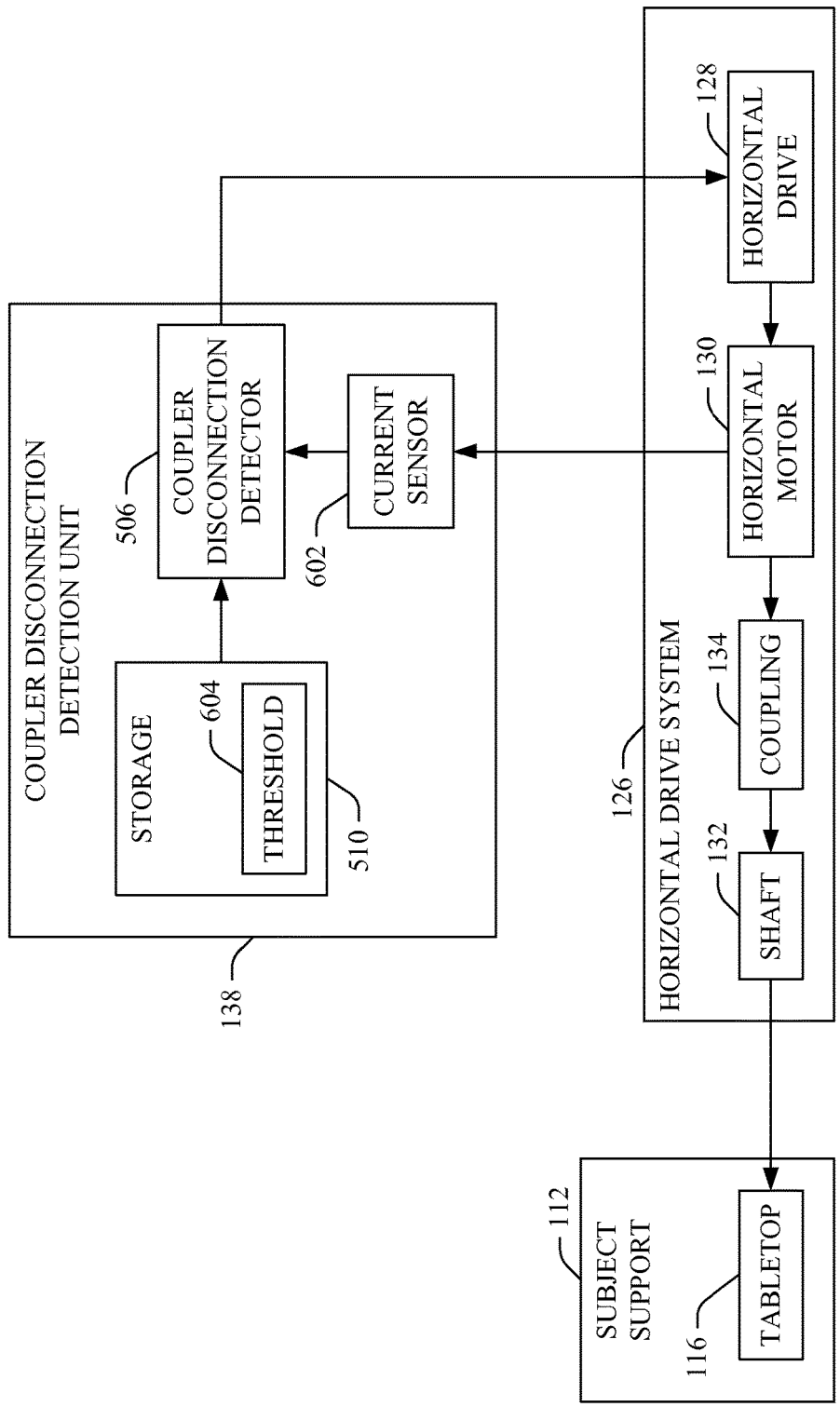
FIG. 6 schematically illustrates example coupler disconnection detection unit having a current sensor and that can be used in connection with the imaging system of FIG. 1.

FIG. 6 schematically illustrates another example of the horizontal drive coupler disconnection detection unit 138 in connection with the horizontal drive system 126 and the subject support 112. With the illustrated example, the screw pitch of the shaft 132 is such that the tabletop 116 back drive force is relatively small, and the inertia of the motor 130 is relatively small. As a consequence, the total system inertia, even without a patient load on tabletop 116, is larger than the total inertia of the motor 130 and the shaft 132 alone. This inertia difference results in a measurable motor electrical current difference between the electrical current draw when the coupler 134 is attached to the motor 130 and the shaft 132 and the electrical current draw when the coupler 134 is detached from at least one of the motor 130 or the shaft 132.

The coupler disconnection detection unit 138 includes an electrical current sensor 602, which senses the electrical current drawn by the horizontal motor 130. The coupler disconnection detector 506 compares the sensed electrical current with a predetermined threshold electrical current 604 stored in the storage 510. The coupler disconnection detector 506, in response to the sensed electrical current meeting or exceeding the predetermined threshold electrical current 604, generates and conveys a signal that causes the horizontal drive 128, in response thereto, to disable or stop driving the horizontal motor 130. A moving average motor current over a predetermined time range can be used to reduce possible effects of motor current noise and control loop tuning. Otherwise, the coupler disconnection detector 506 does not generate and convey the signal, or generates a signal indicating that the sensed electrical current satisfies the predetermined threshold electrical current 604.

Figure 7:
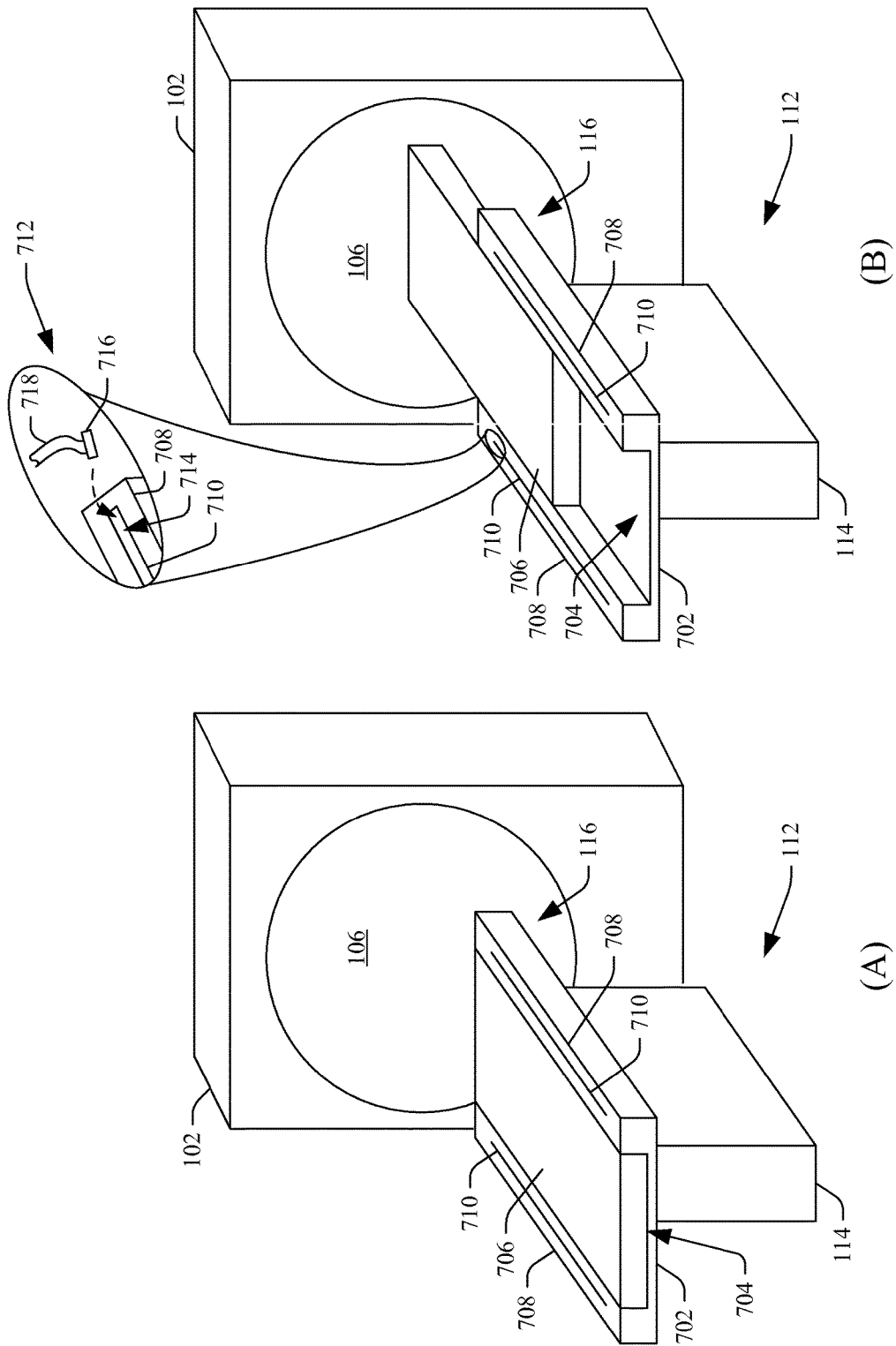
FIG. 7 schematically illustrate an example subject support that can be used in connection with the imaging system of FIG. 1.

FIGS. 7(A) and 7(B) respectively show prospective schematic views of the subject support 112 with the tabletop 116 in a retracted position in which the tabletop 116 is not within the examination region 106 and an extended position in which the tabletop 116 is within the examination region 106.

In the illustrated embodiment, the tabletop 116 includes a cradle 702 stationarily affixed to the base 114 and a recess 704 in which a subject carrier portion 706 is slidably affixed. The subject carrier portion 706 is affixed to the shaft 132 (FIG. 1) of the horizontal drive system 126 (FIG. 1), and the subject carrier portion 706 is driven back and forth within the recess 704 and in and out of the examination region 106 via the horizontal drive system 126 (FIG. 1) as described herein.

In the illustrated embodiment, the subject carrier portion 706 is electrically non-conductive. In one instance, this is achieved through an outer electrically non-conductive surface (e.g., a fiberglass layer, coating or the like) surrounding or enclosing an otherwise electrically conductive or electrically non-conductive core (not shown) at least on a side of the subject carrier portion 706 on which a patient is positioned for scanning. In another instance, the subject carrier portion 706 is formed from an electrically non-conductive material. In yet another instance, an electrically non-conductive apparatus such as a pad, a board, or the like can be placed between the subject carrier portion 706 and a patient on the tabletop 116 such that the patient is only on the electrically non-conductive apparatus.

It is to be appreciated that the electrically non-conductive surface, subject carrier portion 706 and/or apparatus allows for use of a defibrillator or other high voltage or charge producing device with a patient lying on the tabletop 116, for example, with no shock risk to the doctors or nurses or other personnel who would be in contact with the patient table. In another embodiment, the subject carrier portion 706 is a carbon based apparatus which may be electrically conductive. With this embodiment, the subject carrier portion 706 can be electrically grounded or electrically isolated. Additionally or alternatively, the electrically non-conductive apparatus can be used.

The above may be advantageous is various situations such as trauma situations. By way of non-limiting example, where a patient has been transferred to the tabletop 116 to be scanned and the patient's heart stops beating, a defibrillator on a bedside cart or placed on the tabletop 116 can be used to defibrillate the patient without risk of shock to personnel in the examination room that may be in physical contact with the tabletop 116. In configurations in which the tabletop 116 does not include the electrically non-conductive surface, the patient has to be moved from the tabletop 116 to another support in order to mitigate the risk of shock due to an electrically conductive surface of the tabletop 116.

The illustrated cradle 702 includes protrusions 708, one each side of the recess 704, which can be used as additional support for supporting a patient such as arm rests for a patient lying on the subject carrier portion 706. In this embodiment, the protrusions 708 are physically part of the cradle 702. In another instance, the protrusions 708 are part of covers affixed to the subject support 112. In yet another instance, the protrusions 708 are part of accessories which can be connected to and disconnected from the subject support 112 by an operator of the system or other personnel before and/or after each scan. In another embodiment, the protrusions 708 are omitted.

The illustrated protrusions 708 include at least one accessory mounting mechanism 710. In the illustrated example, each of the protrusions 708 includes an accessory mounting mechanism 710. The at least one accessory mechanism 710 can be used for removably mounting an accessory that facilitates scanning and/or maintaining a patient on and/or in a position on the carrier 706. By way of non-limiting example, 712 shows a portion of the accessory mounting mechanism 710 with a slot 714 extending along the long axis of the subject support 112. The slot 714 is configured to receive a connector 716 affixed to an end of an accessory such as a patient restraint accessory 718.

In the illustrated embodiment, the connector 716 is a rectangular member that slides into the slot 714 by turning the member 716 so that the long axis aligns with the long axis of the subject support 112. The member 716 is then turned or rotated to secure the member 716 in the slot 714, thereby securing the patient restraint accessory 718 to the subject support 112. Inside the slot 714, the member 716 is slidable along the long axis, allowing for dynamically and selectively positioning the patient restraint accessory 718 along the long axis. To remove the patient restraint accessory 718, the member 716 is turned so that the long axis aligns with the long axis of the subject support 112 and the member 716 is removed from the slot 714.

The illustrated accessory mounting mechanism 710 and accessory 718 is provided for explanatory purposes and is not limiting. In other embodiments, the accessory mounting mechanism 710 and/or the accessory 718 can be different. For example, the accessory 718 can be any known accessory used with imaging system and/or other accessories, and the accessory mounting mechanism 710 will depend on the type of accessory and approach for securing the accessory to the subject support 112. As one non-limiting example, an alternative accessory mounting mechanism 710 may include a hook and loop type fastener.

Figure 8:
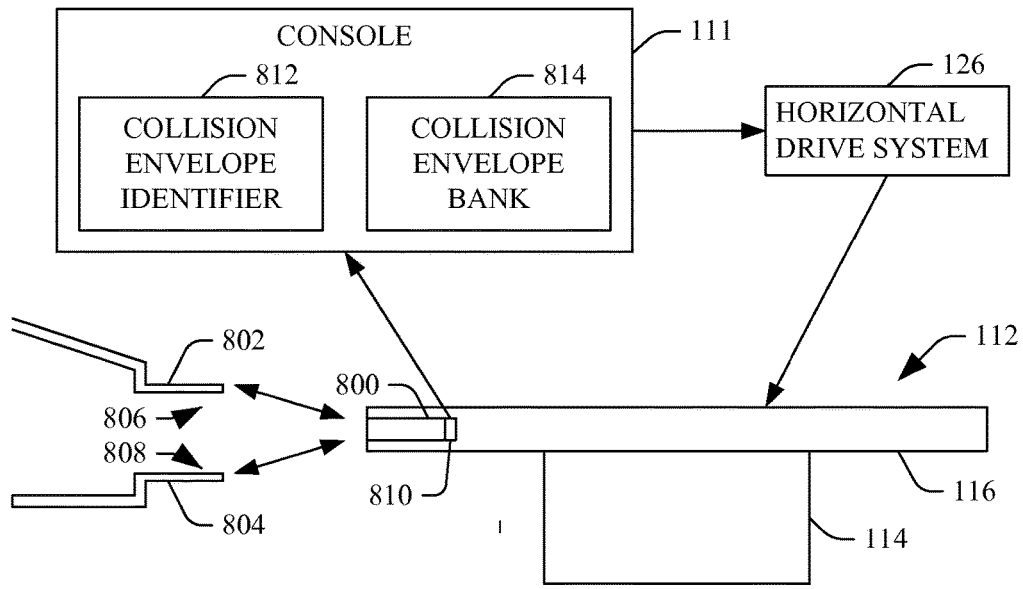
FIGS. 8, 9 and 10 schematically illustrate an example subject support that can be used in connection with the imaging system of FIG. 1.
Figure 9:
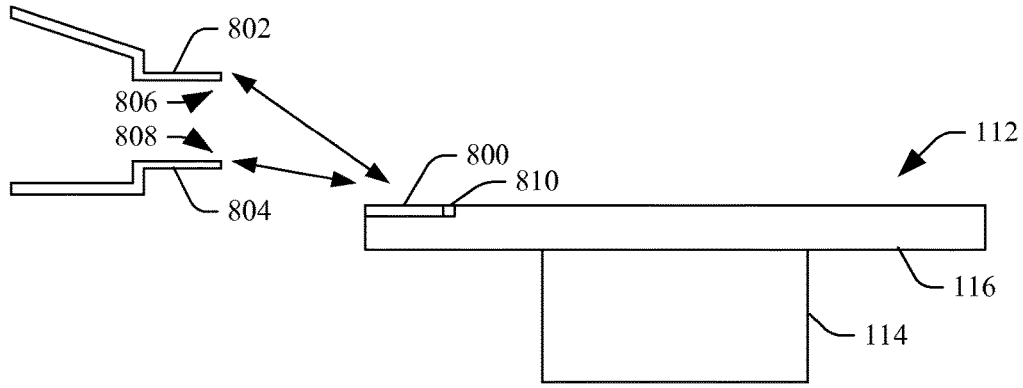
Figure 10:
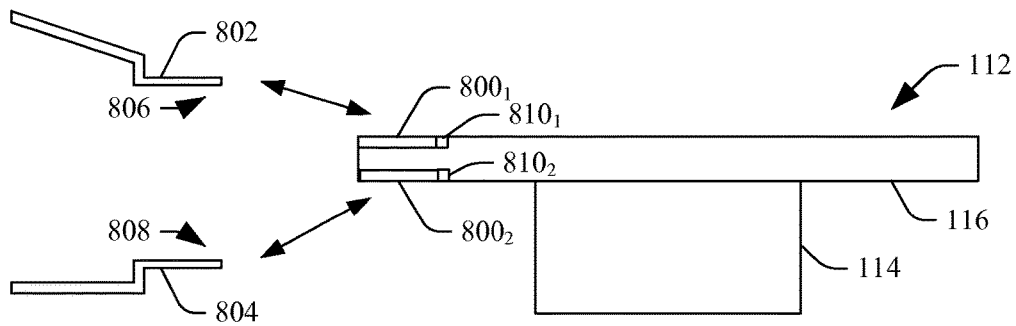

FIGS. 8, 9, and 10 show an additional or alternative subject support accessory mounting mechanism 800 and various accessories such as a foot extender 802, a head rest 804, and/or other accessory.

Initially referring to FIG. 8, the accessories 802 and 804 include ends 806 and 808 configured to couple with the mounting mechanism 800. Either or both, the ends 806 and 808 or the mounting mechanism 800 include a sensor such as an electrical, optical, magnetic, mechanical (e.g., a switch), and/or other sensor. In the illustrated embodiment, a sensor 810 is shown in connection with the mounting mechanism 800. The sensor 810 senses a physical coupling between the end 806 or 808 and the mounting mechanism 800. In response thereto, the sensor 810 sends a signal to the console 111 indicating that an accessory has been attached to the subject support 112.

In the illustrated embodiment, the accessories 802 and 804 include a mechanism which uniquely defines the accessory. For example, the accessory 802 may include a mechanism that uniquely defines it as a headrest or particular headrest, and the accessory 804 may include a mechanism that uniquely defines it as a footrest or particular footrest. In one instance, the mechanism is a physical structure such as a shape, a tab, a recess, etc. In this instance, the sensor 810 is configured to sense the physical structure and generate a signal indicating the physical structure is sensed. In another instance, the accessories 802 and 804 include computer readable memory encoded with data that specifies the type of accessory, a bar code, etc. In this instance, the sensor 810 reads the data from the memory, the bar code, etc. and conveys the data or generates a signal indicative of the data.

In the illustrated embodiment, the console 111 includes a collision envelope identifier 812 and a collision envelope bank 814 with one or more collision envelopes. Generally, a collision envelope defines allowable combinations of vertical and horizontal motion of the base 114 and tabletop 116 so as to mitigate collision of the tabletop 116 and/or a patient thereon with the stationary and/or rotating gantries 102 and 104 and/or other structure. The collision envelope identifier 812 identifies a suitable collision envelope from the bank 814 based on the signal from the sensor 810 and notifies the horizontal drive system 126 of the collision envelope to use for the scan. Where an initial collision envelope is selected based on the selected scan protocol, the signal can be used to override the initial envelope with the envelope identified by the collision envelope identifier 812. The override may be automatic or require user interaction confirming the override. When the accessory is removed, the console 111 may continue using the identified collision envelope, select another collision envelope for use, use a default collision envelope, etc.

In FIG. 8, the mounting mechanism 800 and sensor 810 are shown located within the tabletop 116 and the accessories 802 and 804 plug into the tabletop 116 from the front of the tabletop. In FIG. 9, the mounting mechanism 800 and sensor 810 are located on a top surface of the tabletop 116 and the accessories 802 attaches to the tabletop 116 from the top surface. Alternatively, the mounting mechanism 800 and sensor 810 can be located on a bottom surface of the tabletop 116 where the accessories 802 attaches to the tabletop 116 from the bottom surface. FIG. 10 shows an example in which the mounting mechanism 800 includes a first and a second sub-mounting mechanism 800₁ and 800₂, one located at the top surface and one located at the bottom surface, and each having a corresponding sensor 810₁ and 810₂.

With further reference to FIG. 10, in one instance, as shown, the accessory 802 mounts to the top of the tabletop via the first sub-mounting mechanism 800₁ and the accessory 804 mounts to the bottom of the tabletop via the second sub-mounting mechanism 800₂. In another embodiment, one or more accessories can mount to either of the second sub-mounting mechanism 800₁ and 800₂. Having front, top and/or bottom mounting as described herein, in addition to and/or in alternative to conventional approaches, may allow accessories to be readily mounted and unmounted with the tabletop 116 at essentially any location of the scannable range, with or without having to have a patient re-position themselves on the tabletop 116. This may save time and improve throughput and/or make it more comfortable for patients when adding and removing accessories.

FIGS. 11-16 illustrate various methods in accordance with the above. It is to be appreciated that the ordering of the acts in the methods described herein is not limiting. As such, other orderings are contemplated herein. In addition, one or more acts may be omitted and/or one or more additional acts may be included.

Figure 11:
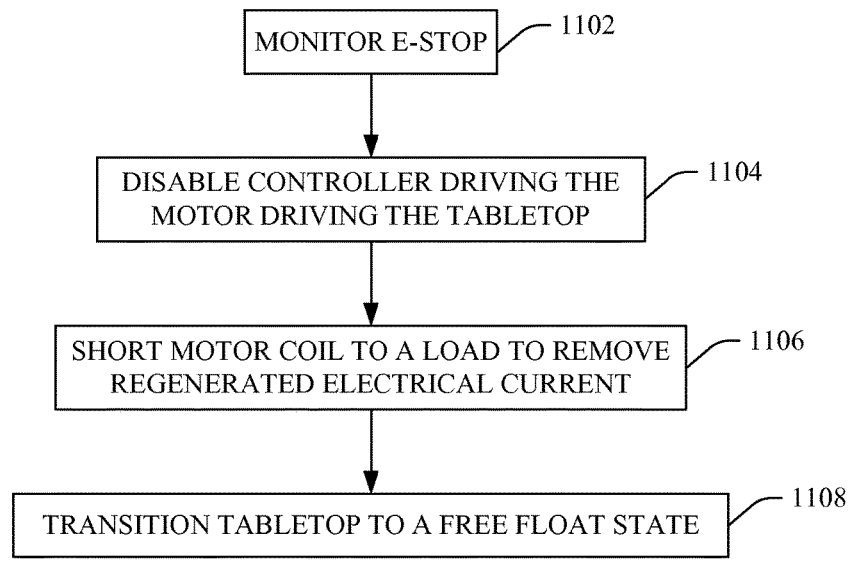
FIG. 11 illustrates a method for stopping tabletop motion in response to controlled or uncontrolled removal of power.

FIG. 11 illustrates a method for stopping a moving tabletop in response to controlled or uncontrolled removal of power.

At 1102, a dedicated emergency stop circuit of an imaging system is monitored. A non-limiting example of such an emergency stop circuit is described in connection with E-stop circuit 140.

At 1104, in response to detecting that the emergency stop circuit tripped, the controller driving the motor that controls tabletop horizontal motion of the subject support of the imaging system is disabled from driving the motor.

At 1106, in further response to detecting that the emergency stop circuit tripped, the coil of the motor driving the tabletop is shorted to a load to remove motor regenerated electrical.

At 1108, optionally, once the tabletop is stopped, the tabletop is placed in a free float state.

The foregoing allows for stopping tabletop motion in accordance with various specifications. By way of non-limiting example, in one instance this allows for stopping the tabletop 116 within 10 or 25 millimeters and a half a second from the time of the event tripping the emergency stop with a patient weighing between 100 and 1000 kg (e.g., 135 kg, 450 kg, 500 kg, etc.) and the tabletop 116 moving at or below 800 mm/s$^2$ (e.g., 450 mm/s$^2$).

Optionally, a physical brake of the motor can be used to facilitate stopping the moving tabletop. In this instance, the brake can be released once the tabletop is stopped so that the tabletop can be placed in the free float state.

Figure 12:
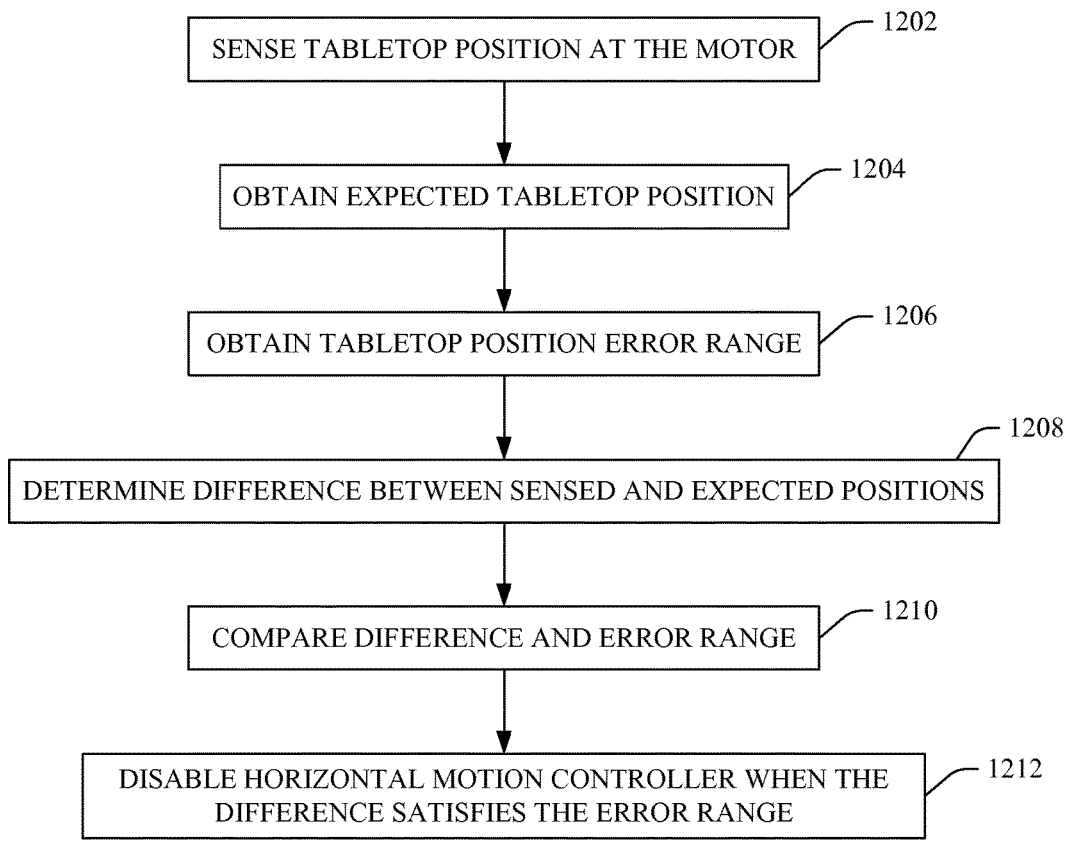
FIG. 12 illustrates a method for mitigating subject support tabletop horizontal collisions.

FIG. 12 illustrates a method for mitigating a tabletop horizontal collision.

At 1202, a tabletop position is sensed via the motor driving the tabletop.

At 1204, an expected tabletop position is obtained.

At 1206, a predetermined position error range is obtained.

At 1208, a difference between the sensed and expected positions is determined.

At 1210, the difference is compared with the error range.

At 1212, if the difference satisfies (e.g., meets and/or exceeds) the error range, the horizontal controller driving the motor driving the tabletop is disabled from driving the motor.

Otherwise, the controller continues driving the motor to drive the tabletop in accordance with the planned motion profile.

Figure 13:
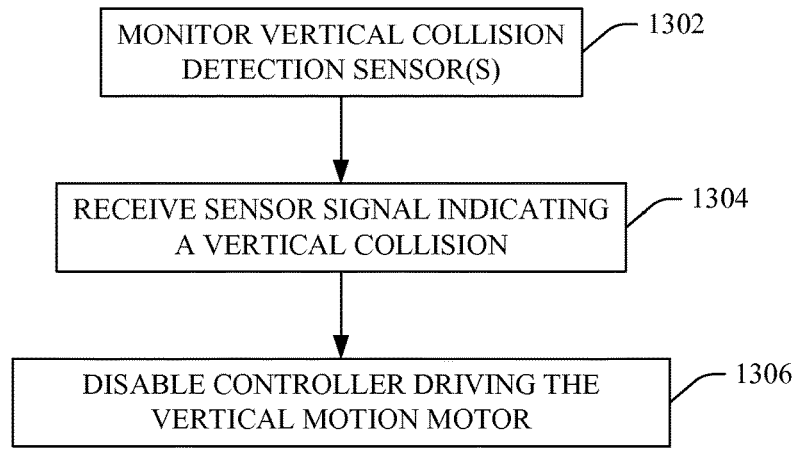
FIG. 13 illustrates a method for mitigating subject support vertical collisions.

FIG. 13 illustrates a method for mitigating a subject support vertical collision.

At 1302, one or more sensors, which are placed between the tabletop of a subject support and the floor to which the base of the subject support is attached, are monitored.

At 1304, receive signal generated by at least one of the sensors in response to the sensor physically contacting an object disposed between the tabletop and the floor.

At 1306, in response to the signal, the controller driving the motor driving the base is disabled from driving the motor.

Figure 14:
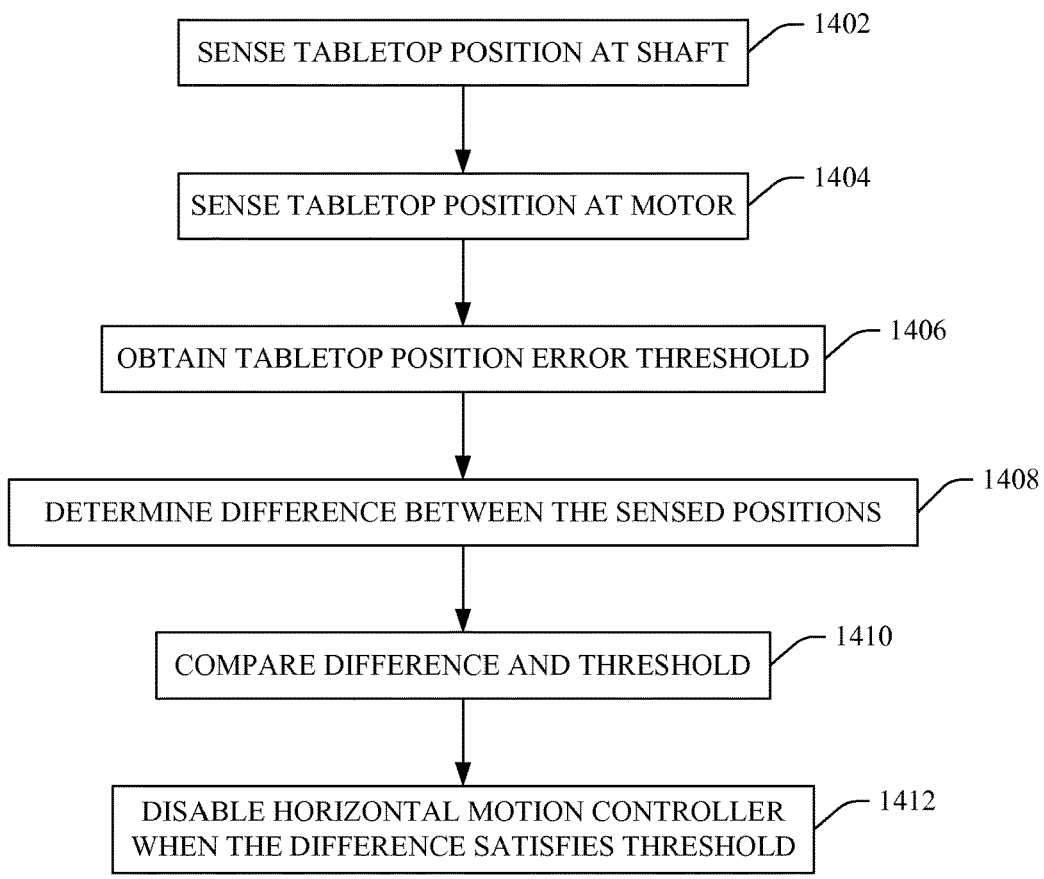
FIG. 14 illustrates a method for detecting horizontal drive system decoupling, using multiple sensors, and disabling or stopping driving of the tabletop in response thereto.

FIG. 14 illustrates a method for detecting horizontal drive decoupling and stopping driving of the tabletop in response thereto using multiple sensors.

At 1402, a first tabletop position is sensed at a shaft coupled to the motor via a coupler.

At 1404, a second tabletop position is sensed at the motor coupled to the shaft via a coupler.

At 1406, a predetermined position error threshold is obtained.

At 1408, a difference between the first and second positions is determined.

At 1410, the difference is compared with the predetermined threshold.

At 1412, if the difference satisfies the predetermined threshold, the horizontal controller driving the motor driving the tabletop is disabled from driving the motor.

Otherwise, the controller continues driving the motor to drive the tabletop in accordance with the planned motion profile.

Figure 15:
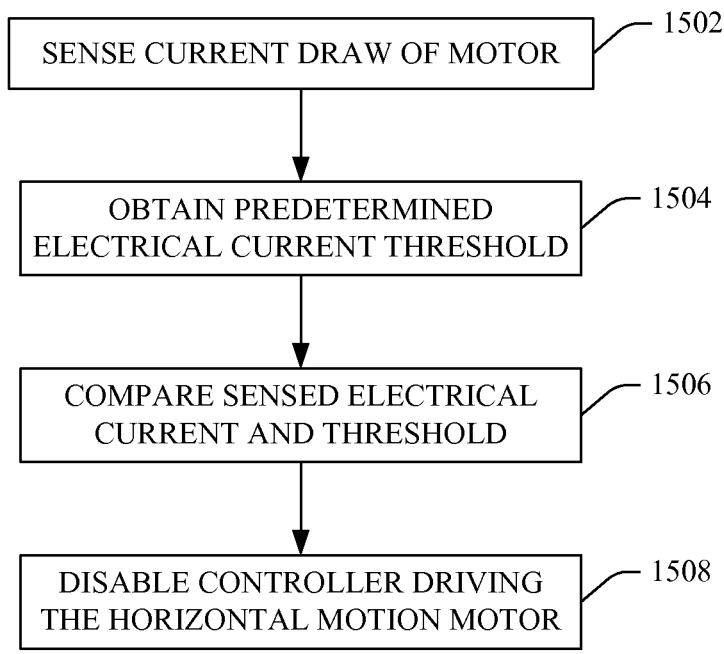
FIG. 15 illustrates a method for detecting horizontal drive system decoupling using a single sensor, and disabling or stopping driving of the tabletop in response thereto.

FIG. 15 illustrates a method for detecting horizontal drive decoupling and stopping driving of the tabletop in response thereto using a single sensor.

At 1502, an electrical current draw of the motor driving the tabletop is sensed.

At 1504, a predetermined electrical current threshold is obtained.

At 1506, the sensed electrical current and the threshold are compared.

At 1508, if the sensed current satisfies the predetermined threshold, the horizontal controller driving the motor driving the tabletop is disabled from driving the motor.

Otherwise, the controller continues driving the motor to drive the tabletop in accordance with the planned motion profile.

Figure 16:
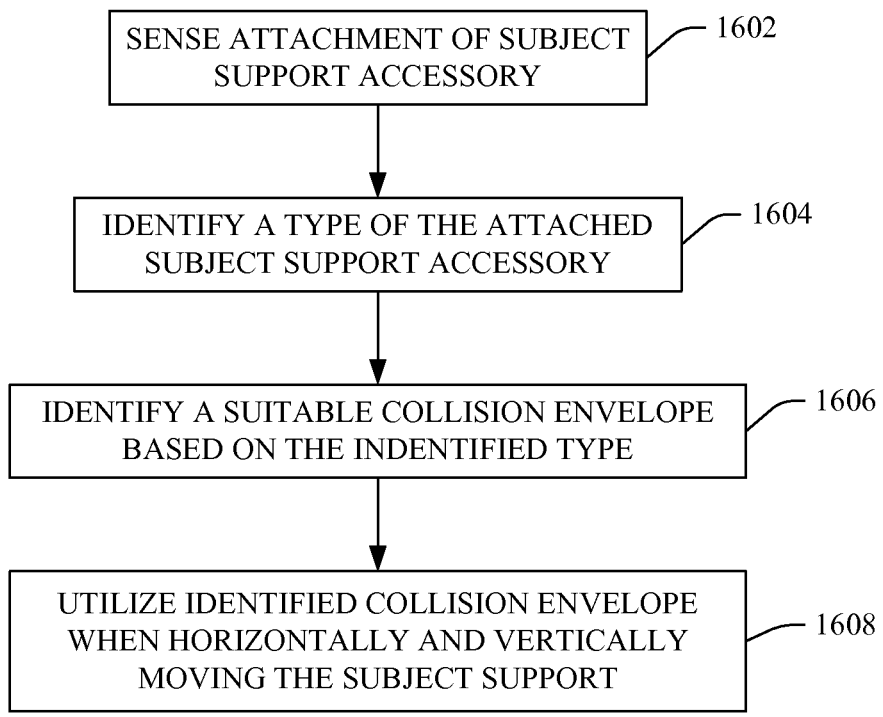
FIG. 16 illustrates a method for detecting physical attachment and/or detachment of subject support accessories and/or identifying a suitable collision envelope based thereon.

FIG. 16 illustrates a method for detecting and/or identifying attachment and/or removal of an accessory to a subject support and/or identifying a subject support collision envelope based thereon.

At 1602, attachment of a subject support accessory is sensed by a sensor of the subject support.

At 1604, a type of the attached subject support accessory is identified.

At 1606, a suitable subject support collision envelope is identified based on the identified type of the attached subject support accessory. As described herein, a suitable collision envelope is one that would avoid a collision between the accessory and the system.

At 1608, the identified subject support collision envelope is utilized to define horizontal and vertical motion ranges when moving the subject support.

Although the above is described in the context of a CT system, it is to be appreciated that it is also amendable to other imaging modalities such as MRI, PET, X-ray, Ultrasound, etc.

It is to be appreciated that the system 100 can be configured to include one or more of the E-stop detection unit 144, the vertical collision prevention unit 124, the horizontal collision prevention unit 136, the coupler disconnection unit 138, and/or other motion preventing, inhibiting, disabling, etc. units. Furthermore, the one or more units can be part of a same component, distributed across components, and/or separated into different components, and that use of the term component herein refers to one or all of the above-noted combinations.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
   receiving a subject support motion disable signal indicative of a need for decoupling of a horizontal motion drive system configured to horizontally drive the tabletop in response to a horizontal collision, wherein the subject support includes a base and the tabletop, which is moveably mounted to base;
   disabling, in response to receiving the subject support motion disable signal, horizontal motion of the tabletop;
   sensing with a sensor attached to the tabletop a physical attachment of a subject support accessory to the tabletop where the subject support accessory is not part of the subject support;
   identifying a type of the subject support accessory based on a mechanism of support accessory that uniquely defines the accessory;
   retrieving and activating a collision envelope for the subject support based on the identity of the subject support accessory; and
   receiving the subject support motion disable signal in response to the subject support moving outside of the collision envelope.

2. The method of claim 1, wherein the motion disable signal is an emergency stop signal, from an emergency stop circuit of the imaging system, indicating power removal, and further comprising:
   disabling, in response to receiving the motion disable signal, a controller of the horizontal motion drive system from driving a motor of the horizontal motion drive system driving the tabletop, wherein the controller is configured to drive the motor to drive the tabletop in accordance with a tabletop motion profile of subject support; and
   removing, in response to receiving the motion disable signal, regenerated electrical current from the motor.

3. The method of claim 2, wherein removing the regenerated electrical current from the motor comprises electrically shorting a coil of the motor to a resistive load.

4. The method of claim 3, further comprising:
   activating, in response to receiving the motion disable signal, a motor brake; and
   releasing the brake after the tabletop has come to a stop, thereby transitioning the tabletop to a free float state in which the tabletop is free to move by applying an external force on the tabletop.

5. The method of claim 2, wherein the tabletop is moving at a velocity between two hundred millimeters per second and one thousand millimeters per second, and, in response to receiving the signal, stopping a moving tabletop within twenty-five millimeters of travel within a half a second from a time of the removal of the power for a tabletop load of one hundred kilograms to five hundred kilograms.

6. The method of claim 2, wherein the tabletop is moving at a velocity between two hundred millimeters per second and one thousand millimeters per second, and, in response to receiving the signal, stopping a moving tabletop within ten millimeters of travel within a half a second from a time of the removal of the power with a tabletop load of one hundred kilograms to five hundred kilograms.

7. The method of claim 1, further comprising:
   receiving a first signal indicative of a horizontal position of the tabletop at a given time, wherein the first signal is sensed via a sensor affixed to a motor shaft of a motor of the horizontal motion drive system;

receiving a second signal indicative of an expected tabletop position at the given time, wherein the expected tabletop position is obtained from a horizontal motion profile of subject support;

determining a difference position signal indicative of a difference between the first and second signals;

obtaining a predetermined position error range;

comparing the difference signal with the error range; and disabling, in response to the difference signal falling outside of the error range, a controller of the horizontal motion drive system from driving the motor, thereby allowing a moving tabletop to coast to a stop.

8. The method of claim 7, wherein the subject support motion disable signal is indicative of only the decoupling of the horizontal motion drive system configured.

9. The method of claim 1, further comprising:

receiving a vertical collision signal indicating the object is located between the tabletop and a floor, wherein the vertical collision signal is from a sensor affixed to the subject support between the tabletop and the floor, and wherein the subject support is affixed to the floor; and disabling, in response to the vertical collision signal falling outside of the error range, a controller of the vertical motion drive system from driving the motor, thereby stopping vertical motion of the subject support.

10. The method of claim 1, wherein the horizontal drive system includes a controller that drives a motor attached to a first end of a drive shaft through a coupler and a second end of the drive shaft is coupled to the tabletop, and further comprising:

receiving a first signal indicative of a horizontal position of the tabletop at a given time, wherein the first signal is sensed via a first sensor sensing position at the shaft;

receiving a second signal indicative of a horizontal position of the tabletop at the given time, wherein the second signal is sensed via a second sensor sensing position at the motor;

determining a difference position signal indicative of a difference between the first and second signals;

obtaining a predetermined position error threshold;

comparing the difference position signal with the predetermined position error threshold; and disabling, in response to the difference position signal meeting or exceeding the predetermined position error threshold, the controller of the horizontal motion drive system from driving the motor, thereby causing a moving tabletop to coast to a stop.

11. The method of claim 10, further comprising:

sensing the first signal with the first sensor sensing position at the shaft;

sensing the second signal with the second sensor sensing position at the motor; and determining the difference position signal meets or exceeds the predetermined position error threshold based on comparing the difference position signal with the predetermined position error threshold.

12. The method of claim 1, wherein the horizontal drive system includes a controller that drives a motor attached to a first end of a shaft through a coupler and another end of the shaft is coupled to the tabletop, and further comprising:

receiving a first signal indicative of an electrical current of the tabletop motor;

obtaining a predetermined electrical current threshold;

comparing the first signal with the predetermined electrical current threshold; and disabling, in response to the first signal meeting or exceeding the predetermined electrical current threshold, the controller of the horizontal motion drive system from driving the motor, thereby causing a moving tabletop to coast to a stop.

13. The method of claim 1, further comprising:

sensing physical attachment of a subject support accessory to the subject support via a sensor attached to the tabletop of the subject support;

identifying a type of the subject support accessory; and performing an action based on the identified type of the subject support.

14. The method of claim 13, further comprising:

identifying a subject support collision envelope, from a plurality of subject support collision envelopes, based on the identified type of the subject support, wherein each of the plurality of collision envelopes defines different horizontal and vertical motion of the subject support; and maintaining motion of the subject support within the identified collision envelope when horizontally and/or vertically moving the subject support with the subject support accessory attached.

15. The method of claim 1, wherein the tabletop includes an electrically non-conductive surface or is electrically grounded or electrically isolated.

16. The method of claim 1, wherein the tabletop includes at least one accessory mounting mechanism for affixing a patient restraint accessory to the subject support so that the patient restraint is secured to the subject support and moveable along a long axis of the subject support.

17. A method, comprising:

sensing, with a sensor attached to a tabletop of a subject support of an imaging system, a physical attachment of a subject support accessory to the tabletop where the subject support accessory is not part of the subject support;

identifying a type of the subject support accessory based on a mechanism of support accessory that uniquely defines the accessory;

retrieving and activating a collision envelope for the subject support based on the identity of the subject support accessory;

receiving a subject support motion disable signal in response to a vertical motion outside of the collision envelope, wherein the subject support further includes a base, and wherein a vertical motion drive system of the subject support drives the subject support vertical motion; and disabling, in response to receiving the subject support motion disable signal subject support vertical motion, a controller of the vertical motion drive system from driving the motor, thereby stopping vertical motion of the subject support.

18. A method, comprising:

sensing, with a sensor attached to a tabletop of a subject support, which includes a base and the tabletop, which is moveably attached thereto, physical attachment of a subject support accessory, which is not part of the subject support, to the subject support;

identifying a type of the subject support accessory based on a mechanism of support accessory that uniquely defines the accessory as one of a headrest or a footrest; and retrieving and activating a collision envelope for the subject support based on the identity of the subject support accessory.

* * * * *